United States Patent [19]

Harris et al.

[11] Patent Number: 4,773,021
[45] Date of Patent: Sep. 20, 1988

[54] ADAPTIVE MODEL-BASED PRESSURE CONTROL AND METHOD OF RESIN CURE

[75] Inventors: Lawson P. Harris, Scotia; Ram K. Upadhyay, Schenectady, both of N.Y.

[73] Assignee: General Electric Company, Schenectady, N.Y.

[21] Appl. No.: 80,355

[22] Filed: Jul. 31, 1987

[51] Int. Cl.⁴ .................. G06F 15/46; G05B 13/02
[52] U.S. Cl. ................... 364/476; 425/143; 425/149; 364/148; 364/149; 364/150; 364/153
[58] Field of Search ............ 364/476, 148, 149, 150, 364/151, 152, 153, 166, 473, 557, 558; 264/40.3; 425/143, 149, 29, 30

[56] References Cited

U.S. PATENT DOCUMENTS

| | | | |
|---|---|---|---|
| 3,819,915 | 6/1974 | Smith | 364/148 |
| 3,985,712 | 10/1976 | Garst | 364/153 |
| 4,373,092 | 2/1983 | Zsolnay | 264/40.3 |
| 4,515,545 | 5/1985 | Hinrichs et al. | 425/143 |
| 4,542,466 | 9/1985 | Arimatsu | 425/29 |
| 4,546,438 | 10/1985 | Prewitt et al. | 364/476 |
| 4,551,807 | 11/1985 | Hsich et al. | 425/30 |
| 4,721,589 | 1/1988 | Harris | 425/143 |

OTHER PUBLICATIONS

R. W. Lauver, "Kinetics of Imidization and Crosslinking in PMR Polyimide Resin", Jr. of Polymer Science: Polymer Chemistry Ed., 17, 2529-2539 (1979).

L. F. Mallett, "Microprocessor-Based Control of Composite Curing", M. S. Thesis, MIT, Jun. 1985.

Primary Examiner—Jerry Smith
Assistant Examiner—Paul P. Gordon
Attorney, Agent, or Firm—Donald R. Campbell; James C. Davis, Jr.; Paul R. Webb, II

[57] ABSTRACT

Composites such as graphite reinforced PMR-15 resin are cured in a heated press by following a temperature schedule and changing from low to high pressure after the start of resin cross linking. A pressure control and method to time application of high pressure uses temperature and dielectric sensor outputs and a semi-empirical model of the resin electrical conductivity. The model estimates the future variation of resin conductivity and determines time-to-go to a maximum in electrical conductivity. A signal to apply high pressure is generated when the estimated time to maximum conductivity falls below a threshold. On-line fitting of the model to sensor data as it is gathered provides a mechanism for adapting the control to the peculiarities of a given batch of resins and a particular cure schedule.

16 Claims, 6 Drawing Sheets

ADAPTIVE MODEL-BASED PRESSURE CONTROL AND METHOD OF RESIN CURE

BACKGROUND OF THE INVENTION

This invention relates to a pressure control system and a method of controlling the curing of certain resins, and adapting the control to the peculiarities of a batch and a particular cure schedule.

Graphite cloth reinforced PMR-15 resin is a high temperature composite material used in aircraft and automobile structures such as aircraft engine guide vanes. A given number of layers of graphite cloth impregnated with these polyimide resins are stacked and cured in a press or autoclave. At lower temperatures and pressures the solvents and water are cooked out and resin imidization takes place, and during a final stage the material is heated under high pressure to a temperature adequate to complete the cross linking reaction. Presently uncontrollable variations in the properties of the resins and/or of the manufacturing cure process used to convert prepreg lay-ups to finished products make it desirable to have a pressure control that applies high pressure to the curing workpiece at a time that depends on the developing properties of the workpiece material. Since sensors are used to measure the material properties, the principal requirements on the control structure are that it be sensor based and provide adaptive control.

Although there is a large body of literature and some commercial practice using such controls and many of the applications involve models of the operation of the controlled plant or desired plant output, no satisfactory technique for curing high temperature composite structures having polymer resins has been developed until now.

SUMMARY OF THE INVENTION

An adaptive, model-based control and method for the application of high pressure during the cross linking of graphite reinforced PMR-15 and other resins is provided by this invention. The control locates a characteristic maximum in the electrical conductivity of the resin-containing material as cross linking occurs and applies the high pressure at a chosen time prior to that maximum. This is selected as a reference in pressure application because it is readily measured and has been shown experimentally to be closely associated with a corresponding minimum in the flow viscosity of the curing resin. Because the composition of the resin may not be closely controlled, the estimate of the time to maximum conductivity is based on on-line measurements and is capable of adapting to the course of each individual cure process. In addition, it was found that the matching of sensed data to a process model permits better estimates. While not essential, the control desirably uses an available dielectrometer system and dielectric sensors.

Briefly, the pressure control system is comprised of sensors and instrumentation for supplying workpiece temperature and resin conductivity data to a control computer during the cure process. Means are provided for computing the predicted future variation of resin conductivity and estimated time to maximum conductivity from a mathematical model (see equations 1 to 3) which utilizes current temperature and conductivity data, precalculated estimates of the fraction of cross linking completed as a function of temperature and time, and current estimates of activation energy and cure constants. There are means to send a signal to the press or other apparatus to apply the high pressure to the workpiece when the estimated time to conductivity maximum drops below a preset threshold. An important feature of the control is that the conductivity model is fitted on-line to currently sensed data; this provides a mechanism to adapt the control to the peculiarities of a given batch of resins and a particular cure schedule. The activation energy constant is adjusted initially and then the cure constant. The sensors are preferably a thermocouple and a dielectric sensor having a parallel plate capacitor structure.

Another feature is data acceptance logic to reject sensed data not in a cross linking range of times and temperatures, and any conductivity data which differs by more than a given factor from the last accepted data. Temperature and conductivity data below preset thresholds are rejected.

Yet another aspect of the invention is a method to control the application of high pressure during the curing and cross linking of a resin-containing material that is heated according to a given temperature schedule. The temperature and electrical conductivity of the material are measured during the cure process. A conductivity model as previously described is provided. The next steps are adjusting the values of the activation energy and cure constants which serve as adjustable parameters in improving agreement between incoming data and model calculations, and computing an estimated time-to-go to the resin conductivity maximum. High pressure is applied when the time-to-go drops below a threshold.

Other features of the method are that when there is acceptable sensor data, the activation energy constant is adjusted until a chosen number of data points are accumulated and the fraction of cross linking completed is above a threshold; then the cure constant is adjusted and time-to-go to conductivity maximum is calculated.

DETAILED DESCRIPTION OF THE INVENTION

Figure 1:
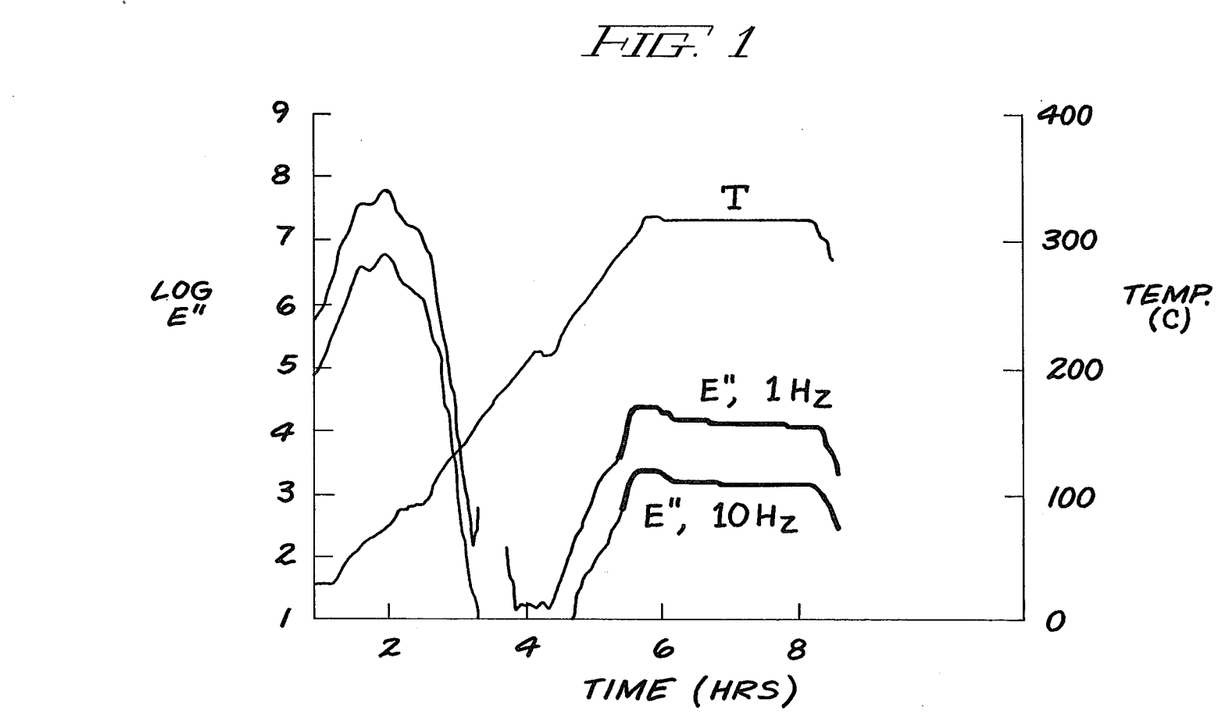
FIG. 1 is a graph showing the variation with respect to time of workpiece temperature, T, and the logarithm of the dielectric loss parameter, E''.

The cure strategy for parts made of graphite cloth reinforced PMR-15 resin is explained briefly with reference to FIG. 1. The resin is a mixture of three components plus a methanol solvent, and is applied to graphite cloth. Impregnated layers are stacked to build the desired part, and the resin is cured in a press or autoclave, both of which heat the part according to a given temperature versus time schedule and apply pressure. In this application, it is desired to apply high pressure to consolidate the part and suppress any gas generation during cross linking after the resin has become sufficiently viscous to resist expulsion from the workpiece under pressure, but before it has become so stiff that it will not flow at all. Experimentally, a maximum in electrical conductivity, measured on-line by a dielectric sensor and microdielectrometer instrumentation, and corresponding nearby minima in the rheological storage and loss parameters are found in the typical PMR-15 cure within the temperature range near 300° C. where most cross linking occurs. A simple model of the cure process indicates that a local conductivity maximum might be expected near where the cross linking process is about half completed. There the increase in charge carrier density associated with the increasing process temperature can be overcome temporarily by a decreasing charge carrier mobility caused by the rapidly increasing cross link density. The electrical conductivity is proportional to the product of charge carrier density and charge carrier mobility.

FIG. 1 shows the variation of measured workpiece temperature (T) and the measured variation of dielectric loss parameter (E") at 1 Hz and 10 Hz frequency. Electrical conductivity is proportional to the dielectric loss parameter. The temperature increases generally linearly up to slightly more than 300° C. and then is held constant, with three breakpoints and holds at about 95°, 210°, and 310°. Examining the cure strategy, at temperatures below 150° C. methanol solvent and water are cooked out and a low pressure is maintained to allow escape of these volatiles. At temperatures between 150° C. and 250° C., there is resin imidization, further methanol and water evolution, and the low pressure is maintained to allow escape of volatiles. At temperatures above 250° C., there is resin cross linking, cyclopentadiene formation, and a high pressure is maintained to consolidate the part and condense volatiles. The electrical conductivity and E" initially rise with temperature, then decrease when the solvents are driven out and the material becomes stiffer. They increase rapidly again as the material starts to melt after resin imidization. During the temperature range of 100° C. to 200° C. there are large variations in the electrical conductivity and E" measurements, with the conductivity again rising after the end of this range. The cross linking reaction starts above 200° C. and conductivity increases to a not very pronounced maximum near 300° C. and then decreases slowly. The darkening of the E" trace indicates the application of high pressure, at a chosen time before reaching the conductivity, maximum; typically the total cure time is 8 hours and high pressure is applied 10–20 minutes before occurrence of the maximum. The pressure control system is operative above 200°–250° C. (conductivity data below this tends to be unreliable). The conductivity maximum is used as a reference in pressure application because it is relatively easily measured, and because experiments have shown that it is closely associated with a corresponding minimum in the flow viscosity of the curing resin.

The pressure control system to time the application of high pressure before the conductivity maximum occurs is sensor-based, model-based, and adaptive. Because the composition of the PMR-15 resin is not closely controlled, it is necessary that the estimate of the time at which the conductivity maximum will occur in any particular cure be based on on-line measurements, and that it be capable of adapting to the course of each individual cure process. In addition, it has been found empirically that the matching of the measured data to a process model permits much better estimates and thus much longer prediction times.

Figure 2:
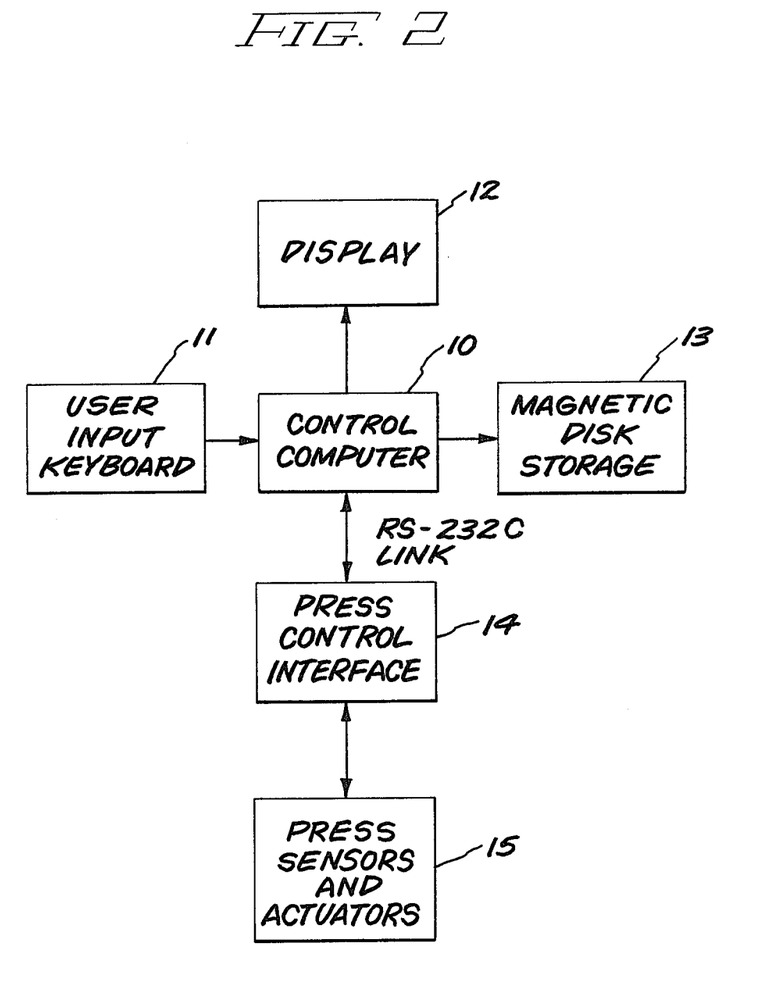
FIG. 2 is a control system block diagram.

A simplified system block diagram of the pressure control is shown in FIG. 2. A control computer 10, actually two computers in this implementation, has the usual user input keyboard 11, display device 12, and magnetic disk storage 13. The latter may store computer programs and log temperature and conductivity data taken throughout a run. The computer has two-way communication via an RS-232C link with the press control interface 14. Block 15 represents the press sensors and actuators which send data to the computer through the interface and receive commands from the computer.

Figure 3:
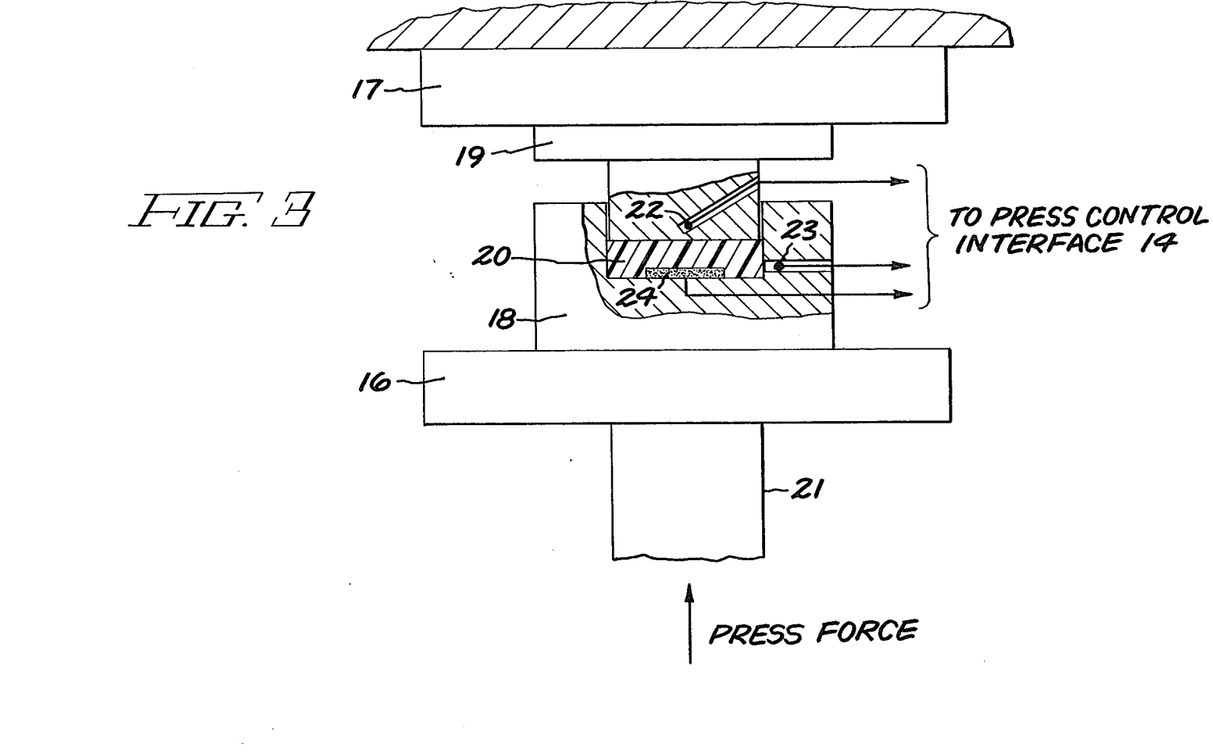
FIG. 3 is a schematic side view of the mold arrangement in the press.

Some of the press parts and the mold arrangement in the press are seen in FIG. 3. The press has lower and upper heated platens 16 and 17 between which the two-part mold 18 and 19 is put. Mold body 18 has a cavity in which the composite workpiece 20 is placed, and mold ram 19 slides inside the cavity pressing on the top of the workpiece. Press force is applied upwardly through column 21 against the lower heated platen. Upper and lower thermocouples 22 and 23 are located in mold ram 19 and mold body 18 and measure workpiece temperature at the top and side of the workpiece 20. Both readings are averaged for the press temperature control, but only the data from lower thermocouple 23 is used by the pressure control system. A dielectric sensor 24 (see FIG. 5 for an enlarged view) measures a loss parameter proportional to electrical conductivity and is placed at the bottom surface of the cavity in mold body 18 in contact with composite workpiece 20. The three sensor signals are fed through press control interface 14 to control computer 10.

Figure 4:
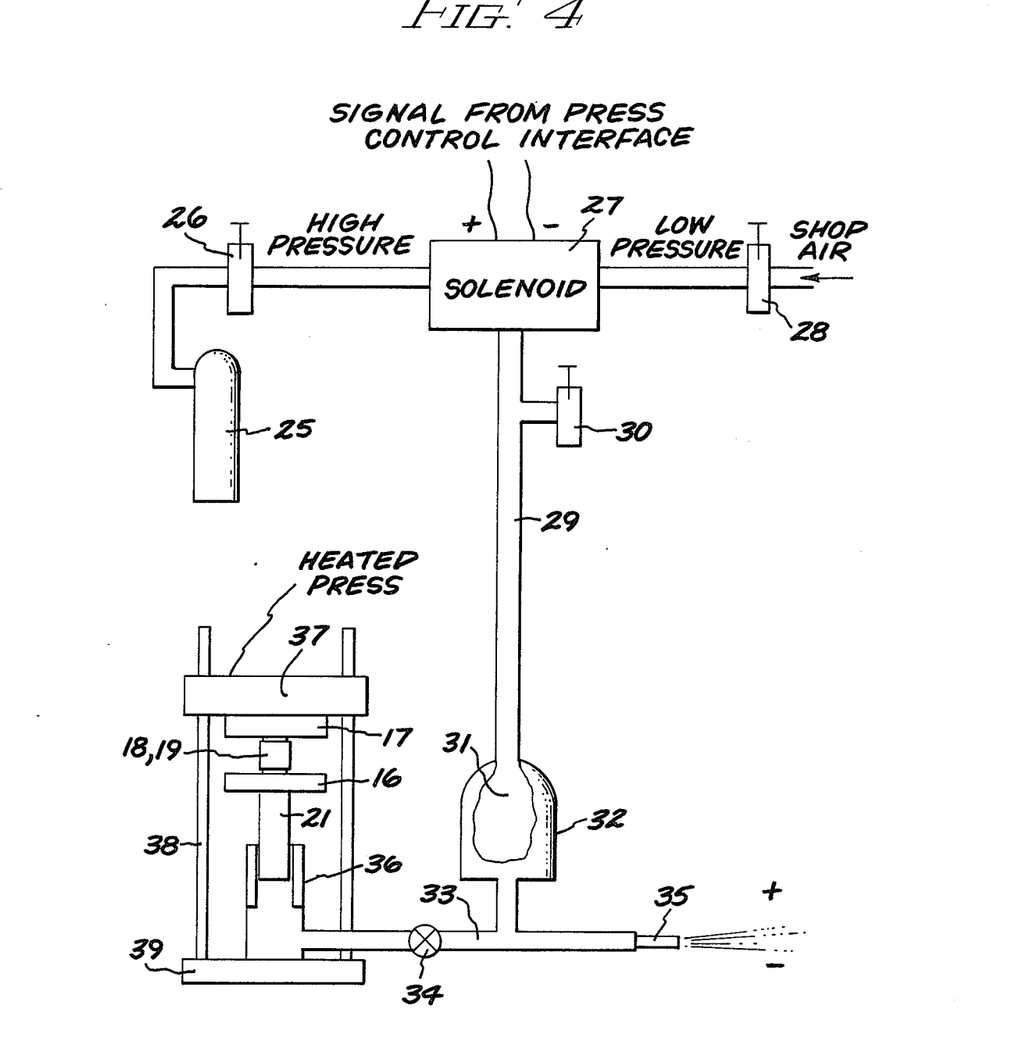
FIG. 4 illustrates schematically the pressure control system for the heated press.

The heated press and pressure application control system are shown in FIG. 4. Nitrogen from a bottle 25 is fed to a regulator 26 and delivered at high pressure (200–500 psi) to an electrically operated solenoid or valve 27. On the low pressure side, shop air flows through a regulator 28 to valve 27 which switches from low to high pressure in response to a signal from the press control interface. One implementation uses a signal from the printer output of control computer 10 without actually going through the press control interface. Fluid passes through a pneumatic line 29, which has a constant leak valve 30, to an expandable bladder 31 which controls passage of hydraulic fluid from an accumulator 32 to the hydraulic line 33. An isolation valve 34 permits the selection of three pressures to be applied to the heated press, high, low and atmospheric pressure. A pressure transducer 35 in the hydraulic line provides a pressure signal to the control computer. Hydraulic fluid admitted to a fluid chamber 36 in the heated press applies force to the end of column 21; this force increases upon the signal from the pressure control system of this invention to apply high pressure to the curing resin at a chosen time before occurence of the conductivity maximum. Other press components in this figure are a horizontal platform 37 that is vertically adjustable on rods 38 supported on the base 39; upper heated platen 17 is secured to the lower surface of this platform.

Figure 5:
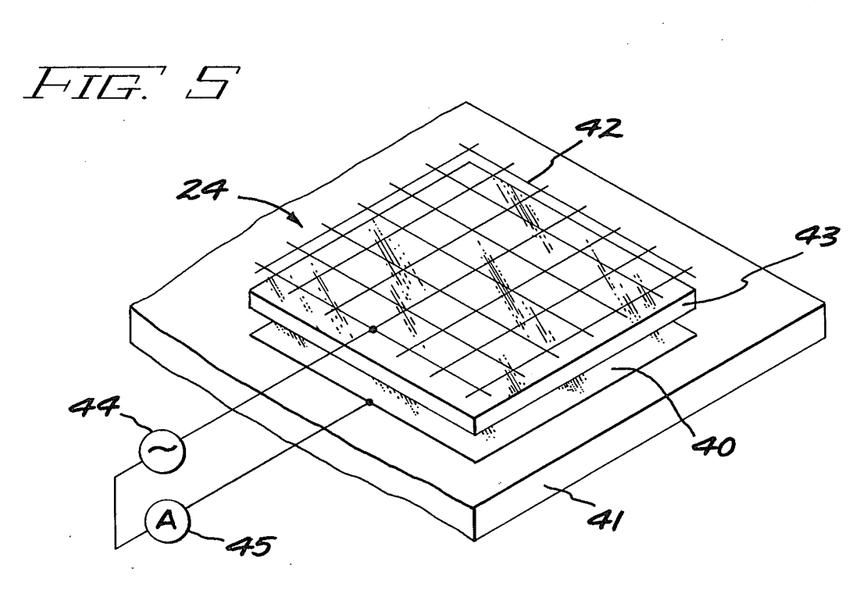
FIG. 5 is an exploded perspective view of the high conductivity dielectric sensor.

Referring to FIG. 5, the dielectric sensor has a parallel plate capacitor structure. It was found that a planar electrode structure did not draw enough current over a sufficient range of measurement conditions to permit accurate and repeatable determinations of current magnitude and phase. The higher conductivity dielectric sensor 24 has a solid electrode 40 on a substrate 41 which is separated from the upper wire mesh electrode 42 by a porous insulating spacer 43. The liquid resin gets in between the wires of the top electrode and through the insulating layer to the lower electrode. The sensor must be protected from graphite fibers, however, by an overlay of glass cloth or felt. An AC source 44 excites the sensor with a sinusoidal signal, 1-10 KHz, typically 1 to 100 Hz. Current is measured by associated dielectrometer instrumentation indicated at 45. Measurements of electrical conductivity of the PMR-15 resin largely free of noise or error over most of the resin cure temperature range, and over more than six decades range in conductivity magnitude, are obtained. To explain the dielectrometer measurements principle, the resin-containing sensor is modeled as a lossy capacitor such that upon applying a sinusoidal excitation voltage the resistance leakage is measured. It can be shown that the dielectric loss parameter E" is equal to the resistive admittance divided by the vacuum capacitive admittance; $E'' = \sigma/\omega\epsilon_o$, where $\omega$=electrical conductivity, $\omega$=frequency, and $\epsilon_o$=space permittivity. The measurements depend primarily on the conductance of the resin and/or the sensor insulation.

This pressure control system uses conductance measurements of the dielectric sensor which are fitted to a mathematical conductivity model to predict the location in time of a resin conductivity maximum. On-line fitting of the model to the sensor data as it is gathered provides a mechanism for adapting the control to the peculiarities of a given batch of resins and a particular cure schedule.

THE CONDUCTIVITY MODEL

The conductivity model used here can be described mathematically by $$\sigma = \sigma_o \exp\left[-E\left(\frac{1}{T} - \frac{1}{T_o}\right) - C(\alpha - \alpha_o)\right], \quad (1)$$

where $\sigma$, T, and $\alpha$ are the electrical conductivity, absolute temperature, and fractional completion of the cross linking reaction, respectively, of the PMR-15 resin, and the subcripts o refer to a reference condition just prior to the start of the cross linking reaction. The quantity E is an empirical constant proportional to the activation energy of the cross linking reaction and having units of temperature. The constant C is a dimensionless empirical constant. Both E and C are used as adjustable parameters in fitting this conductivity model to data. This model, which was developed by one inventor and subsequently was shown to permit acceptable fits to measured electrical conductivity data, is not intended for general use but rather for the restricted range of cure conditions where the cross linking reaction is dominant. Equation 1 may be described as a modified Arrhenius equation; the last term is a modification to account for the rate of cross linking.

It is convenient to use the capability of the control computer to calculate logarithms of the experimental data to gain working variables that vary linearly with the adjustable coefficients in the model. Taking logarithms of both sides of Equation 1 gives $$\ln(\sigma) = \ln(\sigma_o) - E\left[\frac{1}{T} - \frac{1}{T_o}\right] - C(\alpha - \alpha_o) \quad (2)$$

In this equation, the term proportional to E gives a steady increase in $\ln(\sigma)$ as temperature increases. The term proportional to C, however, can cause a local maximum in $\ln(\sigma)$ as temperature increases because the fractional cure $\alpha$ increases rapidly from values near zero to values near unity as the temperature passes through the characteristic temperature for the cross linking reaction. Differentiation of the last equation with respect to temperature gives $$\frac{d}{dt}\ln(\sigma) = \frac{E}{T^2}\frac{dT}{dt} - C\frac{d\alpha}{dt} \quad (3)$$

According to the model, a peak in electrical conductivity will occur when the right side of this equation becomes zero. A peak might occur if $dT/dt \to 0$ even for modest $d\alpha/dt$, but occurrence of a conductivity peak while the temperature is increasing strongly requires rapidly increasing $\alpha$.

The foregoing model requires a value of $\alpha$, the fraction of the cross linking reaction completed, which cannot be measured easily. It is calculated for each individual cure from the cross linking model given in the Appendix.

Figure 6:
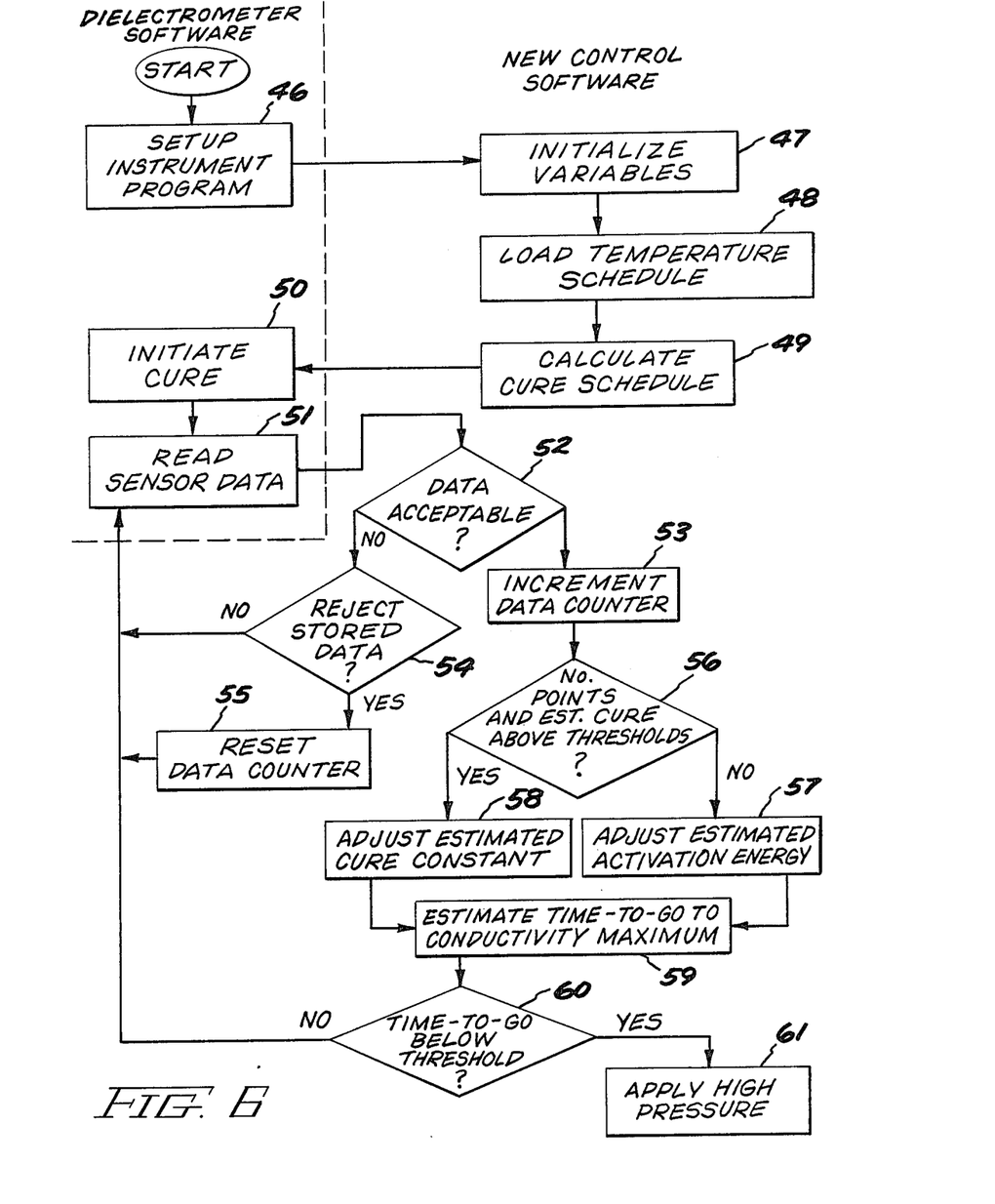
FIG. 6 is a flowchart of existing dielectrometer instrumentation software and new control software showing the principal steps in deriving the time to apply high pressure to the press.

The pressure control system is implemented with a program in BASIC language for use with Micromet Instruments, Inc. Eumetric® Microdielectrometer System II hardware, software, and P3 dielectric sensor (the latter is shown in FIG. 5). The control program for gathering data from that instrument, performing extrapolations in accord with the models, and generating a signal for controlling high pressure application in the cure of graphite/PMR-15 composites has six BASIC subroutines and a few interfacing statements. They are intended to be merged with the Micromet copyrighted BASIC program PCMON used in the collection of information from Micromet dielectric sensors by an IBM PC computer during composites processing. The Micromet program reads the temperature, applies test voltages, and measures currents frox the dielectric sensor. In FIG. 6, the existing microdielectrometer system software is at upper left and the remainder is the new control software.

Referring to FIG. 6, at the start as shown at step 46 the Micromet program is set up and there is a shift to the new software beginning with the interfacing statements. Among these, step 47, are initializing variables such as setting flags, and counters and time-to-go to a conductivity maximum to initial values. Other interfacing statements may be to call the new program, send instructions to the display, and select channels for conductivity data processing and temperature measurements.

The control program continues, at step 48, by calling for the loading of a temperature schedule for the part being processed. This is a schedule of temperatures versus time, approximately corresponding to the workpiece temperature measurements shown in FIG. 1, and is obtained from the process engineer. The temperature schedule depends primarily on the part geometry. The temperature schedule includes the breakpoints or holds of the piecewise linear time/temperature cure schedule.

The program next calculates, at step 49, the cure schedule, using calls to a piecewise linear interpolation subroutine and a fractional cure calculation subroutine. Since ordinarily the points at which the calculated cure is wanted do not coincide with the breakpoints of the temperature schedule, it is necessary to interpolate temperatures at times between these breakpoints. The fraction of cross linking completed is calculated using a BASIC implementation of the cross linking model given in the Appendix, Equations 4–10. The results are a table of fractional cure expected as a function of temperature and time. Calculation of each point of the cure schedule takes a second or more, and for this reason is done off-line before the start of the composite cure. An accuracy of about 1% is adequate. The cure schedule is based on the scheduled temperatures rather than the temperatures actually achieved during the cure, but there is a feedback control on the process temperature and the penalty is minor. Rate of change of temperature and cure fraction may be calculated and stored.

There is a shift back to the Micromet program at steps 50 and 51 to initiate the cure and turn on the press heaters, and read data on workpiece temperature and conductivity provided by thermocouple 23 and dielectric sensor 24. The control program screens the sensor data and determines, at step 52, if the data is acceptable. Because only data in the cross linking range of times and temperatures are of interest here, and because the period just prior to cross linking usually produces low values of conductivity seriously contaminated by electrical noise, the data are filtered by data acceptance logic in this subroutine to reject unsuitable values where possible. Thresholds on temperature, conductivity, calculated fractional cure, and on the number of points (temperature and conductivity) already accepted, are used in this logic. One example is that no points are accepted at temperatures below 473° K. or for measured conductivities such that the logarithm (base 10) is less than $-11$. In addition, any conductivity datum that differs by more than a factor of ten from the last accepted value is rejected, and two such successive out of range readings cause all earlier accepted data to be discarded, and the data accummulation process to begin anew, i.e., the data counter is reset. Thus at steps 53–55, a data counter is incremented when there is an acceptable data point. If the variation from the last data is not excessive, the next sensor data is read and tested to see if it is above the set thresholds. When the first conductivity datum is accepted, an estimate may be made of the time-to-go until conductivity maximum using Equation 3 with values of $\alpha$ from the calculated cure schedule and default values of activation energy and cure constants E and C, 14,000 K and 2.5, respectively. No change is made in that initial estimate until later.

Referring to steps 56–59, the activation energy constant E is initially adjusted, and then the cure constant C to improve agreement between incoming data and model calculations based on Equation 2. When the number of accepted data points and the estimated cure fraction are below their thresholds, set at 5 points and 0.03 cure fraction, each accepted data point after the first produces a call to the subroutine for activation energy calculation to adjust the activation energy E from its stored value. During this initial stage, the value of C is held at the default value. The activation energy constant calculation is based on Equation 2, and an estimate of the change in $\ln \nu$ from its value for the first accepted datum is made using the model Equation 2, and this estimate is compared with the actual value found from the data. The calculated value of E is then adjusted part of the way, 50%, from its currently stored value to the value that would make the model calculation agree with the last experimental reading. After the number of accummulated data points exceeds the threshold (5 points) and the calculated cure fraction exceeds its threshold (0.03), the stored value of E is frozen, and each new conductivity datum results in a call to the subroutine for cure constant calculation, to adjust the stored value of C to improve agreement between incoming data and the model calculations. Using a similar algorithm, an estimate of the change in $\ln \nu$ from its value for the first accepted datum is made using the model Equation 2, and this estimate is compared with the actual value found from the data. The value of C is then adjusted 60% of the way from its currently stored value to the value that would make the model calculation agree with the last accepted data. Once the adjustment of cure constant C starts, new estimates of time-to-go to conductivity maximum are made after each new datum is accepted.

Although fluctuations in the estimates of time-to-go are common among the first few estimates, the computed values usually settle to a nearly linearly decreasing curve pointing to a conductivity maximum at a fixed absolute time. When the estimate of time-to-go falls below the set threshold, steps 60 and 61, a signal is generated and sent to the heater apparatus (solenoid 27 in FIG. 4) to apply high pressure to the workpiece.

In conclusion, the adaptive pressure control system and method of controlling application of high pressure is sufficiently flexible and reliable to be useful in manufacturing operations. The control adapts automatically to a given batch of resins and cure schedule; there is on-line fitting of the resin conductivity model to sensor data as it is taken.

APPENDIX

THE CROSS LINKING MODEL

The fitting of the preceding conductivity model to experimental data requires estimation of the degree of cross linking $\alpha$. The calculation of this cure fraction is derived from analysis of curves of cure fraction vs. time for PMR-15 measured by Lauver (Journal of Polymer Science: Polymer Chemistry Edition, 17, 2529–2539 (1979). In those experiments, the cross linking. temperature was maintained constant. The empirical fit to Lauver's data is given by the expression $$\frac{d\alpha}{dt} = \begin{cases} (A + 2Bt)(1 - \alpha), & 0 \leq t \leq t_m \\ Z(1 - \alpha), & t_m \leq t \end{cases} \quad (4)$$

where A,B,Z are functions of T only and $t_m$ is a curve matching time independent of temperature. Because $d\alpha/dt$ must be continuous at $t_m$, only two of the three parameters A,B,Z, are independent, and they must satisfy the relation $$A + 2Bt_m = Z. \quad (5)$$

The appearance of time explicitly in Equation 4 complicates the use of this model, for that time refers to time in an isothermal experiment and is different from running time in a typical cure process.

To derive the variation of $\sigma$ over short periods (between tabulated points of a look-up table), Equation 4 can be integrated to yield $$-\ln(1-\alpha) = \begin{cases} At + Bt^2, & 0 \leq t \leq t_m \\ -\ln(1-\alpha_m) + Z(t-t_m), & t_m \leq t \end{cases} \quad (6)$$

In particular, the upper expression in Equation 6 gives for $t=t_m$ $$-\ln(1-\alpha_m) = At_m + Bt_m^2$$

Since $t_m$ is a known constant and A and B are known functions of temperature, this equation can be solved to give $\alpha_m$ as a function of temperature $$\alpha_m = 1 - \exp(-At_m - Bt_m^2). \quad (7)$$

If $\alpha < \alpha_m$, the upper expression in Equation 6 holds and it can be solved to calculate the isothermal experiment time $t^*$ corresponding to any given value of cure fraction $\alpha^*$, $$t^* = -\frac{A}{2B} - \left[\left(\frac{A}{2B}\right)^2 - \frac{\ln(1-\alpha^*)}{B}\right]^{\frac{1}{2}}, \alpha^* < \alpha_m \quad (8)$$

The minus sign is taken before the square root because B is a negative quantity (A<Z) and the smaller of the two possible positive solutions for $t^*$ is realized physically. (The slope of the curve of $-\ln(1-\alpha)$ vs. t does not reverse in the range $t^\circ t_m$.) The cure fraction existing a short time $\delta=(t-t^*)$ after $t^*$, while T is essentially constant, can be calculated from $$-\ln(1-\alpha) = -\ln(1-\alpha^*) + A(t^*+\delta) + B(t^*+\delta)^2,$$
$$\alpha^* \leq \alpha_m. \quad (9)$$

If $\alpha > \alpha_m$, the lower expression in Equation 6 holds, and the rate of change of cure fraction depends only on the temperature. Then the variation of cure fraction during a short essentially isothermal period of length $\delta$ after $\alpha = \alpha^*$ is obtained from $$-\ln(1-\alpha) = -\ln(1-\alpha^*) + Z\delta \quad (10)$$

Equations 9 and 10 account properly for the changes in $d\alpha/dt$ during the time interval $\delta$, in accord with Equation 4, but are restricted to periods during which the temperature T is essentially constant, as is Equation 4.

While the invention has been particularly shown and described with reference to preferred embodiments thereof, it will be understood by those skilled in the art that changes in form and details may be made without departing from the spirit and scope of the invention.

The Invention claimed is:

1. An adaptive model-based pressure control system for an apparatus in which a resin-containing workpiece is cured by heating according to a given temperature vs. time schedule and applying a low pressure during initial stages of the cure and a high pressure after the start of resin cross linking, comprising:
   sensors and associated instrumentation for supplying workpiece temperature and resin conductivity data to a control computer during the cure process;
   said control computer having means for computing the predicted future variation of resin conductivity and estimated time to a conductivity maximum from a mathematical model which utilizes current temperature and conductivity data, precalculated estimates of the fraction of cross linking completed, and activation energy and cure constants; and
   means for sending a signal to said apparatus to apply said high pressure to said workpiece when the estimated time to conductivity maximum drops below a preset threshold.

2. The pressure control system of claim 1 further comprising means for fitting said mathematical model on-line to said current data.

3. The pressure control system of claim 2 wherein said last-mentioned means is comprised of means for adjusting said activation energy constant initially, and thereafter adjusting said cure constant and recalculating the estimated time to conductivity maximum.

4. The pressure control system of claim 2 wherein said computer has data acceptance logic to reject said current data not in a cross linking range of times and temperatures and which differs by a given factor from the last data.

5. The pressure control system of claim 2 wherein said sensors are a thermocouple and a dielectric sensor having a parallel plate capacitor structure.

6. An adaptive pressure control system for a heated press in which a graphite cloth reinforced PMR-15 resin workpiece is cured by following a given temperature vs. time schedule and applying low pressure during initial stages of the cure and high pressure after the start of resin cross linking, comprising:
   means for sensing workpiece temperature and resin conductivity and supplying sensor data to a control computer during the cure cycle; said control computer having:
   means for precalculating from a cross linking model an estimate of the fraction of cross linking reaction completed as a function of temperature and time;
   means for computing the predicted future variation of resin conductivity and estimated time to a conductivity maximum from a mathematical model which utilizes current temperature and conductivity data, the fraction of cross linking completed, and activation energy and cure constants that are adjusted on-line to fit said model to said current data; and
   means for sending a signal to said heated press to apply said high pressure to said workpiece when the estimated time to conductivity maximum drops below a preset threshold.

7. The pressure control system of claim 6 wherein said sensing means are a thermocouple and a high conductivity dielectric sensor having a parallel plate capacitor structure.

8. The pressure control system of claim 7 further comprising means for rejecting said sensor data not in a cross linking range of times and temperatures and any conductivity data that differs by more than a given factor from last accepted data.

9. A method to control application of high pressure during the curing and cross linking of a resin-containing material that is heated according to a given temperature schedule, comprising:
   continuously measuring the temperature and electrical conductivity of said material during a cure process;
   providing a conductivity model to predict future variation of resin conductivity from currently sensed temperature and conductivity data, a precalculated estimate of the fraction of cross linking completed, and activation energy and cure constants;

adjusting the values of said constants which serve as adjustable parameters in improving agreement between incoming data and model calculations;

computing an estimated time-to-go to a resin conductivity maximum; and applying said high pressure to said material when the time-to-go is below a threshold.

10. The method of claim 9 wherein said conductivity model is expressed mathematically by:

$$\sigma = \sigma_o \exp\left[-E\left(\frac{1}{T} - \frac{1}{T_o}\right) - C(\alpha - \alpha_o)\right],$$

where $\sigma$, T, and $\alpha$ are the electrical conductivity, absolute temperature, and fractional completion of the cross linking reaction, respectively, of the resin, subscripts o refer to a reference condition just prior to the cross linking reaction, E is the activation energy constant, and C is the cure constant.

11. The method of claim 9 further comprising rejecting unsuitable values of said incoming data not in a cross linking range of time and temperature.

12. The method of claim 11 further comprising adjusting the activation energy constant E until an acceptable number of data are accumulated and the fraction of cross linking completed is above a threshold, then adjusting the cure constant C and calculating the time-to-go to conductivity maximum.

13. The method of claim 9 further comprising rejecting any temperature and conductivity data points that are below thresholds and not in a cross linking range, and any conductivity data that differs excessively from a last accepted value.

14. The method of claim 13 further comprising adjusting only said activation energy constant, starting with a default value, until a given number of acceptable data points are accumulated and the calculated fraction of cross linking completed is above a threshold, and thereafter adjusting only said cure constant and calculating the time-to-go to conductivity maximum.

15. The method of claim 9 wherein said material being cured is a fiber-reinforced resin.

16. The method of claim 9 wherein said material being cured is graphite cloth reinforced PMR-15 resin.

* * * * *